United States Patent [19]
Sasaki et al.

[11] Patent Number: 5,626,574
[45] Date of Patent: May 6, 1997

[54] DISPOSABLE DIAPER

[75] Inventors: Tohru Sasaki; Toshifumi Ohtsubo, both of Kawanoe, Japan

[73] Assignee: Uni-Charm Corporation, Ehime-ken, Japan

[21] Appl. No.: 354,134

[22] Filed: Dec. 6, 1994

[30] Foreign Application Priority Data

Dec. 10, 1993 [JP] Japan .................. 5-066021 U

[51] Int. Cl.$^6$ .................................................. A61F 13/15
[52] U.S. Cl. .................................... 604/385.2; 156/190
[58] Field of Search ................. 156/190; 604/385.1, 604/385.2

[56] References Cited

U.S. PATENT DOCUMENTS

| | | | |
|---|---|---|---|
| 2,729,010 | 1/1956 | Markus et al. | 156/290 |
| 2,899,349 | 8/1959 | Jenkins | 156/290 |
| 2,992,958 | 7/1961 | Yamaguchi | 156/290 |
| 2,999,042 | 9/1961 | Meister | 156/290 |
| 3,221,738 | 12/1965 | Ekberg et al. | 156/290 |
| 3,932,260 | 1/1976 | Balentine, Jr. | 156/290 |
| 4,070,513 | 1/1978 | Rhoads | 156/290 |
| 4,326,902 | 4/1982 | Peddie | 156/290 |
| 4,752,349 | 6/1988 | Gebel | 156/290 |
| 4,919,738 | 4/1990 | Ball et al. | 156/290 |
| 4,938,817 | 7/1990 | Langley | 156/290 |

FOREIGN PATENT DOCUMENTS

| | | | |
|---|---|---|---|
| 5-15551 | 1/1993 | Japan . | |
| 1332037 | 10/1973 | United Kingdom | 156/290 |

*Primary Examiner*—Michael J. Milano
*Attorney, Agent, or Firm*—Lowe, Price, LeBlanc & Becker

[57] ABSTRACT

A disposable diaper of pants type having front and rear bodies bonded to each other by series of welded zones along transversely opposite sides of front and rear waist sections, wherein the welded zones are at least partially defined by patterns of V-shape or patterns of V-shape being devoid of a sharp point, both laid down transversely of the diaper, or patterns of an arc opening transversely of the diaper.

6 Claims, 4 Drawing Sheets

FIG.I

DISPOSABLE DIAPER

BACKGROUND OF THE INVENTION

The present invention relates to a disposable diaper, more particularly to a disposable diaper formed in pants type.

It is well known for disposable diapers formed in pants type comprising heat-weldable top- and backsheets to seal front and rear bodies to each other by means of heat welding along transversely opposite sides of front and rear waist sections. For example, Japanese Laid-Open Patent Application No. 1993-15551, of which the applicant is the same as the applicant of the present application, discloses a sealing technique for pants type diapers, by which a series of intermittent rectangular welded zones each having a long side extending in parallel to a waist line of the diaper are longitudinally arranged along each lateral side of the front and rear waist sections utilizing an ultrasonic welding. Use of this technique enables the diaper put on a wearer to be easily stripped off merely tearing off the diaper along the sealed side edges of the diaper. This technique is advantageous also in that the interior of the diaper is always maintained in good communication with the exterior of the diaper and thereby the diaper of high air-permeability is obtained.

Tearing off tends to take place along a peripheral edge of each welded zone as the diaper is torn off. The sheets usually used to form the diaper comprise a thin nonwoven fabric or a plastic film of a relatively small weight per unit area and a correspondingly low tear strength, since, after the sheets have been welded to each other, the welded zone exhibits a tear strength higher than that exhibited by the nonwelded zone and a tearing force is concentrated along a boundary between the welded zone and the nonwelded zone. Consequently, there is an apprehension that a tear might progress circumferentially, i.e., transversely into the front and/or rear bodies as the diaper is torn off along the long side of each rectangular welded zone, instead of being torn longitudinally of the diaper. Such undesirable phenomenon will readily occur particularly when both the top- and backsheets exhibit a lower tear strength in transverse direction significantly than a tear strength in longitudinal direction. Unless the diaper is torn off in the longitudinal direction, it will be impossible to relieve the wearer from the diaper as quickly as possible.

Accordingly, a principal object of the invention to solve the problem as has been mentioned above by providing a diaper with welded zones at least partially defined by patterns each having contours diverging transversely of the diaper so that the diaper may be easily torn off along such contours obliquely downwards.

SUMMARY OF THE INVENTION

To achieve the object set forth above, the invention broadly resides in a disposable diaper comprising a liquid-permeable topsheet, a liquid-impermeable backsheet sandwiched between these two heat-weldable sheets, and having front and rear bodies sealed to each other along transversely opposite sides of front and rear waist sections, defined by portions extending outwards from transversely opposite side edges of said liquid-absorbent core in said front and rear bodies by series of intermittent welded zones arranged longitudinally along the respective waist side portions.

The invention is characterized in that the welded zones are at least partially defined by patterns each having an outer contour formed substantially in a V-shape laid down transversely of the diaper, said outer contour comprising that of an arc opening transversely of said diaper as a modified form thereof.

With the disposable diaper constructed as has been described above, the top- and backsheets are torn off obliquely along contours of each welded zone diverging transversely of the diaper, instead of being torn off circumferentially of the waist, as the waist side portions are torn off.

BRIEF DESCRIPTION OF THE DRAWINGS

The invention will be readily apparent from the following description of preferred embodiments in reference with the accompanying drawing, in which.

PREFERRED EMBODIMENTS OF THE INVENTION

Figure 1:
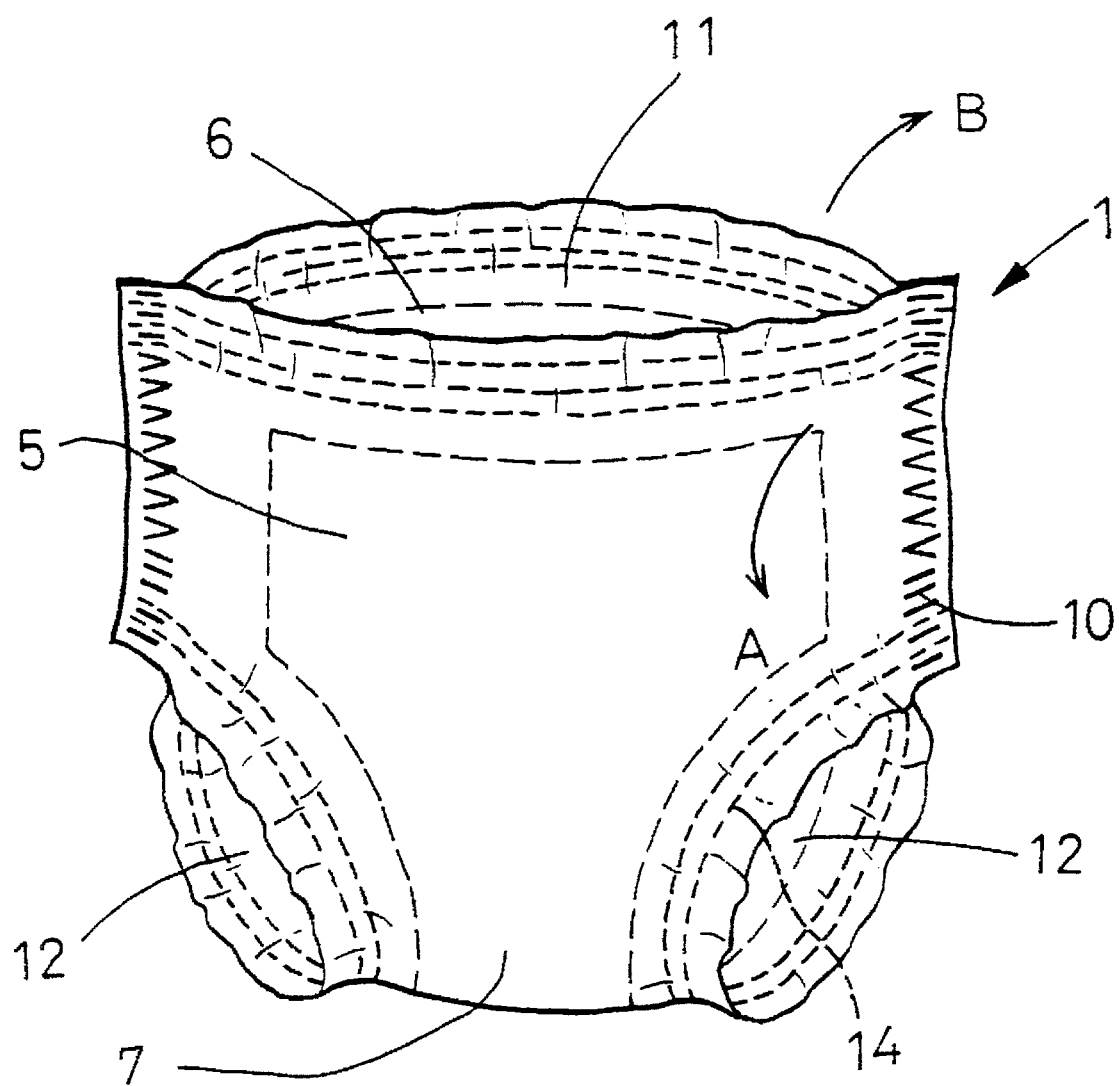
FIG. 1 is a perspective view showing a disposable diaper.
Figure 2:
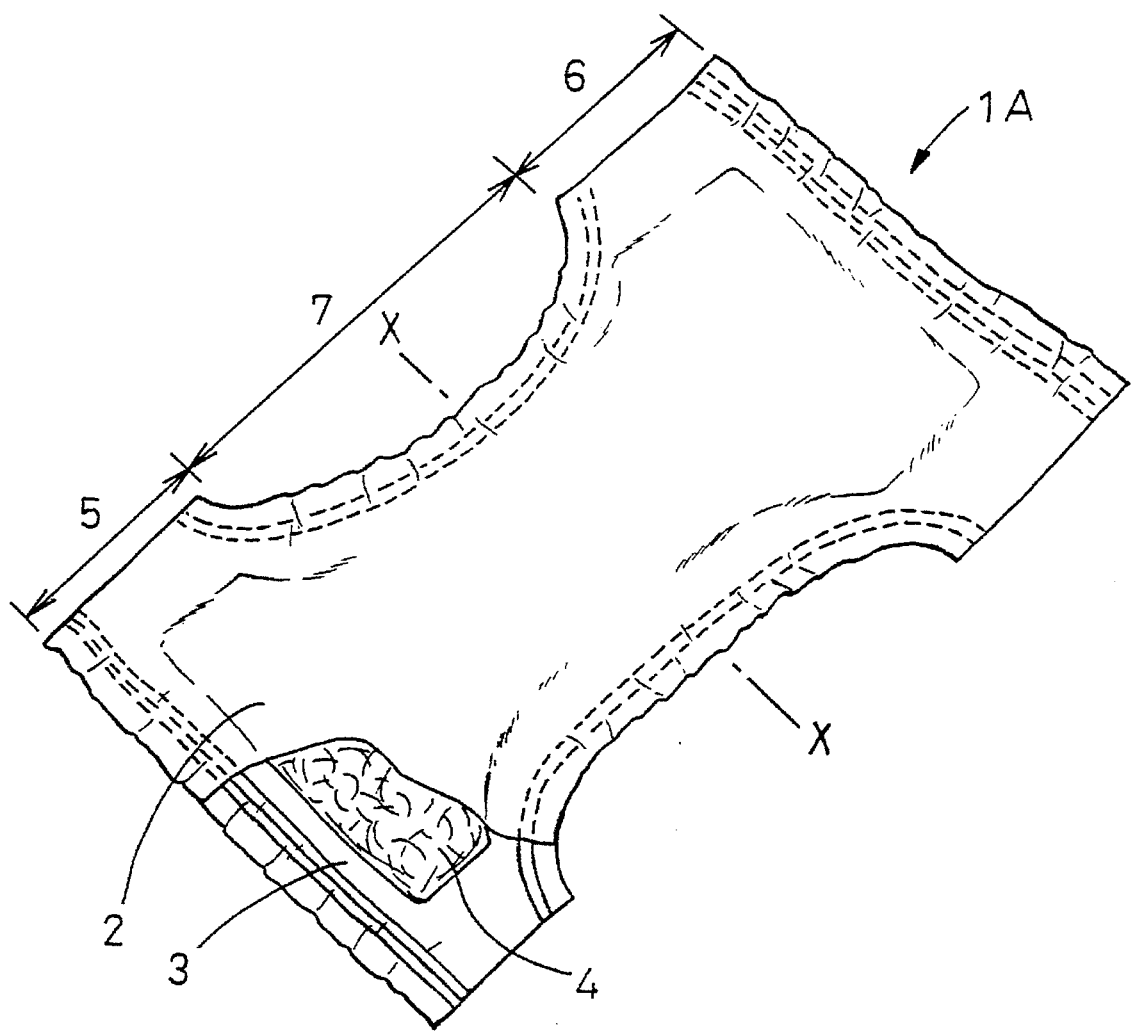
FIG. 2 is a perspective view showing the diaper as developed in longitudinal direction.

Referring to FIGS. 1 and 2, a blank 1A of a diaper 1 comprises a liquid-permeable topsheet 2, a liquid-impermeable backsheet 3 and a liquid-absorbent core 4 sandwiched between these two sheets 2, 3, and is generally composed of a front body 5, a rear body 6 and a crotch zone 7. The topsheet 2 is formed by a nonwoven fabric of thermoplastic fibers, the backsheet 3 is formed by a thermoplastic film, and these two sheets 2, 3 are heat-weldable to each other. Referring to FIG. 2, portions of the top- and backsheets 2, 3 extending outwards from the peripheral edge of the liquid-absorbent core 4 are itermittently bonded to each other by means of adhesive (not shown) in the diaper blank 1A. The diaper blank 1A may be folded inwards in two along a longitudinally middle line X—X and transversely opposite side edges of the front and rear bodies 5, 6 formed by portions of the top- and backsheets 2, 3 extending outwards from transversely opposite side edges of the liquid-absorbent core 4 and lying one upon another may be sealed together by series of welded zones 10 intermittently provided along the respective side edges to form the diaper 1 into pants type. The diaper 1 thus formed has a waist-opening 11 and a pair of leg-openings 12. These openings 11, 12 are provided along their peripheries with a plurality of parallel elastic members 13, 14 bonded to said peripheries, respectively, in their stretched condition.

Figure 3:
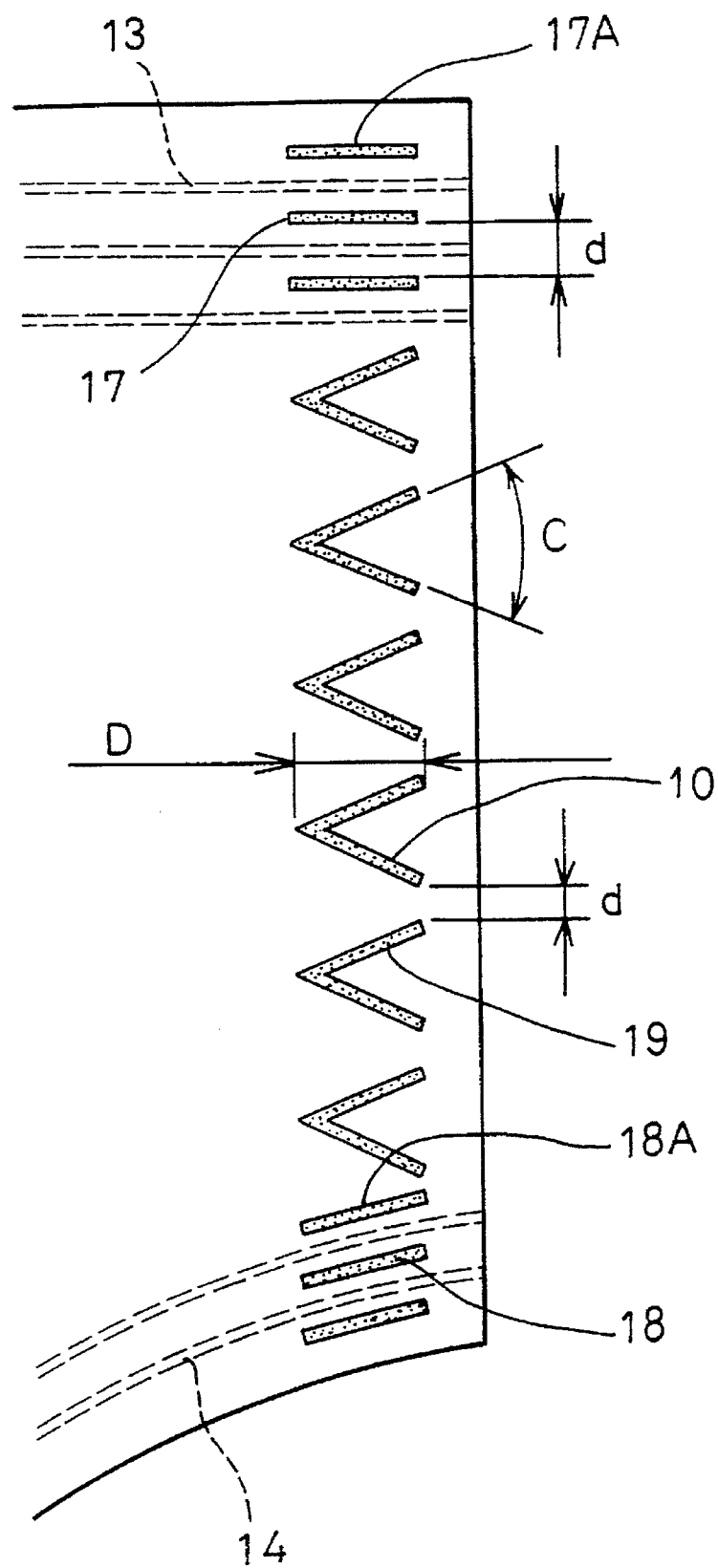
FIG. 3 is a fragmentary plan view showing an embodiment of welded zones in the diaper in an enlarged scale.

Referring to FIG. 3, the elastic members 13 shown in the upper portion of the waist side edge is associated with the waist-opening 11 and the elastic members 14 shown in the lower portion of the waist side edge is associated with the leg-openings 12. The welded zones 10 comprise first rectangular welded patterns 17 intermittently provided between each pair of adjacent the elastic members 13 for the waist-opening and adjacent the uppermost elastic member 13 and having their long sides 17A extending in parallel to the elastic members 13, second rectangular welded patterns 18 intermittently provided between each pair of adjacent the elastic members 14 for the leg-openings and adjacent the lowermost elastic member 14 and having their long sides 18A extending in parallel to the elastic members 14 and third laid down V-shaped welded patterns 19 intermittently provided between the lowermost elastic member 13 and the uppermost elastic member 14. Each of said first and second welded patterns 17, 18 is a rectangular welded zone dimensioned to be 0.3 to 2×3 to 10 mm (height×length) and each of the third welded patterns 19 is a V-shaped welded zone described by a welded line being 0.3 to 1.5 mm wide and dimensioned to have an included angle C=15 to 90° and a length D=3 to 10 mm. All of the welded patterns 17, 18, 19 are spaced by d=0.5 to 3 mm one from another and non-welded zones defined between each pair of adjacent patterns contribute to promote a fluid communication between interior and exterior of the diaper, improving the desired air-permeability of the diaper.

With the diaper 1 shown by FIG. 1, the diaper 1 can be torn off longitudinally down along the welded zones 10 by pulling the front and rear bodies 5, 6 in directions as indicated by arrows A, B with the waist-opening gripped in hands and thereby a wearer can be easily relieved from the diaper 1. The welded zones 10 of the diaper 1 generally have a tear strength higher than that of the top- and backsheets 2, 3, so the top- and backsheets 2, 3 are torn off along the outer peripheries of the first, second and third welded patterns 17, 18, 19 as the front and rear bodies are pulled in the directions A, B. In other words, the top- and backsheets 2, 3 tend to be torn off transversely along the first and second welded patterns 17, 18 and tend to be torn off in V-shape along each of the third welded patterns 19 and thereby to be obliquely downwards torn off in zigzags along the series of V-shaped patterns 19. Particularly when fibers and/or polymers in the top- and backsheets 2, 3 are oriented transversely of the diaper 1 and these sheets 2, 3 tend to be torn off transversely of the diaper due to such orientation, there is an apprehension that the sheets 2, 3 might be torn off along the first and second welded patterns 17, 18 into the front and/or rear bodies. However, according to this embodiment of the diaper 1, the first and second welded patterns 17, 18 are located as adjacent as possible to the elastic members 13 for the waist-opening and the elastic members 14 for the leg-openings so that such apprehension may be minimized and the major portions of the respective waist side edges are sealed only by the third welded patterns 19 so that the top- and backsheets 2, 3 may be easily torn off longitudinally but not transversely of the diaper 1. While it is possible to replace the first and second welded patterns 17, 18 by the third welded patterns 19, the V-shaped patterns 19 might cross and cut the elastic members 13, 14 or the elastic members 13, 14 might impede quick welding of the top- and backsheets 2, 3 depending on the distance by which the elastic members 13, 14 are spaced one from another, respectively.

Figure 6:
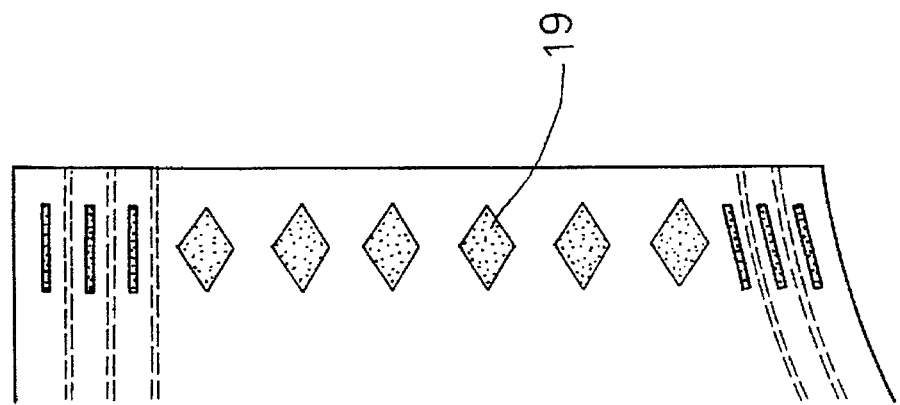
FIG. 6 is a view similar to FIG. 3 showing still another embodiment of the welded zones.
Figure 5:
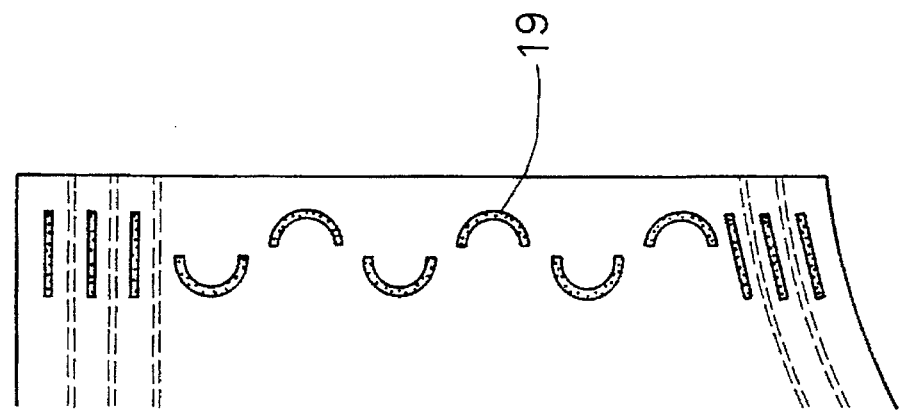
FIG. 5 is a view similar to FIG. 3 showing another embodiment of the welded zones.
Figure 4:
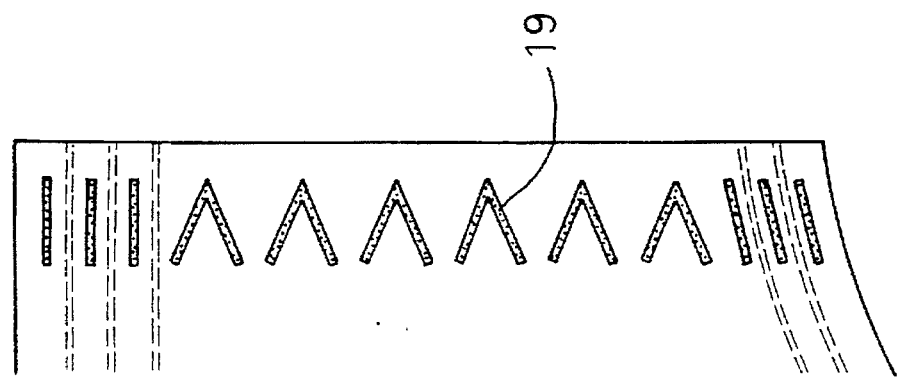
FIG. 4 is a view similar to FIG. 3 showing another embodiment of the welded zones.

FIGS. 4, 5 and 6 are views similar to FIG. 3 showing various embodiments of the third welded pattern 19. Referring to FIG. 4, the laid down V-shaped third welded pattern 19 diverges towards the center of the diaper 1. The V-shape may be devoid of its sharp point. Referring to FIG. 5, the third welded pattern 19 is an arc opening transversely of the diaper 1 and its orientation is alternated, which is a modified form of the V-shaped pattern 19 shown in FIGS. 3 and 4. Referring to FIG. 6, the third welded pattern 19 is a rhombus formed by two laid down V-shaped contours one of which diverge towards the center of the diaper 1 and the other diverge in the opposite direction. While the third welded patterns 19 may be continuous one to another, instead of being intermittently arranged as exemplarily shown by FIGS. 3 through 6, such continuous arrangement of the third welded patterns 19 will deteriorate the air-permeability of the diaper 1.

According to the invention, the heat-weldable top- and backsheets 2, 3 may be subjected to embossing or ultrasonic welding to obtain the first, second and third welded patterns 17, 18, 19. The topsheet 2 may be formed by a nonwoven fabric made of thermoplastic fibers or a porous thermoplastic film and the backsheet 3 may be formed by a thermoplastic film, a nonwoven fabric or a laminate of a nonwoven fabric and a plastic film. The liquid-absorbent core 4 may be formed by the well known materials conventionally used for this component.

In the disposable diaper according to the invention, the front and rear bodies are welded together along the transversely opposite side edges of the front and rear waist sections and this welding is achieved by the welded zones comprising the intermittent patterns each having contours of V-shape or V-shape devoid of its sharp point, both laid down transversely of the diaper or patterns each having contours of circular arc opening transversely of the diaper. Accordingly, when the diaper is torn off along the waist side edges to relieve a wearer from the diaper, the top- and backsheets are torn off obliquely downwards along said contours rather than being torn off circumferentially of the waist. In this manner, no failure of tearing off occurs.

What is claimed is:

1. A disposable diaper comprising:

a liquid-permeable topsheet;

a liquid-impermeable backsheet;

a liquid-absorbent core sandwiched between said topsheet and said backsheet;

the topsheet, backsheet and core forming a front body and a rear body, said front and rear bodies separated longitudinally by a crotch zone;.

the diaper having front and rear bodies seamed to each other by a series of intermittent welded zones having first and second side edges and arranged along transversely opposite side portions of said front and rear bodies, the transversely opposite side portions being defined by portions of the front and rear bodies extending outwardly from transversely opposite side edges-of said core;

the diaper having a plurality of elastic members along peripheries of at least one of a waist-opening and a pair of leg openings, wherein a first generally rectangular weld pattern including a plurality of intermittent generally rectangular welds is provided at said transversely opposite side portions of said front and rear bodies with one of said plurality of intermittent rectangular welds disposed between pairs of adjacent elastic members with long sides of the first generally rectangular welds generally parallel to the elastic members; and wherein welded patterns define each of said welded zones, each welded pattern having an outer contour portion defined by outer edges, said outer edges being spaced apart at said second side edge and being connected to each other at said first side edge;

the combination of rectangular welds and welded patterns along the intermittent welded zones permitting the diaper to be torn off a user longitudinally along the welded zones.

2. A disposable diaper according to claims 1, wherein said outer contour portion is formed substantially in a V-shape laid down transversely of the diaper.

3. A disposable diaper according to claim 2, herein said V-shape is devoid of a sharp point.

4. A disposable diaper according to claim 1, wherein said outer contour portion is formed in an arc shape opening transversely of the diaper.

5. A disposable diaper according to claim 1, wherein said outer contour portion is formed in a rhombus.

6. A disposable diaper according to claim 1, wherein said welded zones defined by said patterns are provided between uppermost one of elastic members provided along peripheries of a waist-opening of the diaper and lowermost one of elastic members provided along peripheries of leg-openings of the diaper.

* * * * *